(12) United States Patent
Awad et al.

(10) Patent No.: US 9,491,947 B1
(45) Date of Patent: Nov. 15, 2016

(54) METHOD OF SYNTHESIZING NANOPARTICLES AND A NANOPARTICLE-POLYMER COMPOSITE USING A PLANT EXTRACT

(71) Applicant: KING SAUD UNIVERSITY, Riyadh (SA)

(72) Inventors: Manal Ahmed Gasmelseed Awad, Riyadh (SA); Awatif Ahmed Hendi, Riyadh (SA); Nada Elzain Eisa, Riyadh (SA); Khalid Mustafa Osman Ortashi, Riyadh (SA); Nada Mohammed Merghani, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/868,367

(22) Filed: Sep. 28, 2015

(51) Int. Cl.
| | | |
|---|---|---|
| *B01J 13/20* | (2006.01) | |
| *A01N 59/16* | (2006.01) | |
| *C01G 23/053* | (2006.01) | |
| *A01N 25/34* | (2006.01) | |
| *A01N 25/10* | (2006.01) | |
| *B22F 9/24* | (2006.01) | |
| *B22F 1/00* | (2006.01) | |

(52) U.S. Cl.
CPC ............ *A01N 59/16* (2013.01); *A01N 25/10* (2013.01); *A01N 25/34* (2013.01); *B01J 13/206* (2013.01); *B22F 1/0044* (2013.01); *B22F 9/24* (2013.01); *C01G 23/053* (2013.01); *C01P 2004/51* (2013.01); *C01P 2004/64* (2013.01)

(58) Field of Classification Search
CPC ..................................................... B01J 13/206
See application file for complete search history.

(56) References Cited

FOREIGN PATENT DOCUMENTS

WO    WO2005/085339    9/2005

OTHER PUBLICATIONS http://dspace.jdvu.ac.in/bitstream/123456789/24347/1/Acc.%20No.%20DC%20822.pdf , 2012.*
Mbhele et al., "Fabrication and Characterization of Silver-Polyvinyl Alcohol Nanocomposites," Chem. Mater., 2003, 15, pp. 5019-5024. Abstract.
Palomba et. al., "Activities of Antimicrobial Silver Polystyrene Nanocomposites," J. of Nanomaterials, 2012, pp. 1-7.

* cited by examiner

*Primary Examiner* — Carlos Azpuru
(74) *Attorney, Agent, or Firm* — Richard C. Litman

(57) ABSTRACT

A method of synthesizing nanoparticles using a plant extract can include providing a first solution comprising a metal salt or a metal oxide, providing a second solution including extract from orange peel, and combining the first solution and the second solution to produce a nanoparticle solution including metal nanoparticles or metal oxide nanoparticles. The nanoparticle solution can be used to produce a crystal nanoparticle powder, a non-crystal nanoparticle powder, and/or a metal-polymer nanocomposite wherein the polymer is polystyrene (PS) or poly-vinyl alcohol (PVA).

8 Claims, 12 Drawing Sheets

METHOD OF SYNTHESIZING NANOPARTICLES AND A NANOPARTICLE-POLYMER COMPOSITE USING A PLANT EXTRACT

BACKGROUND OF THE INVENTION

1. Field of the Invention

The present invention relates to synthesis of nanoparticles and a nanoparticle-polymer composite using a plant extract, and particularly to synthesis of metal and metal oxide nanoparticles using orange peel extract.

2. Description of the Related Art

Nanoparticles exhibit completely new or improved properties compared to corresponding bulk materials. The differences in properties can be attributed to the variation in size, morphology and distribution of the particles. Metal nanoparticles, in particular have distinctive features, including catalytic, optical, magnetic and electrical properties. Metal nanoparticles are conventionally obtained from metal salt solutions in the presence of a chemical reducing agent and a stabilizing agent, which serves to prevent nanoparticles from aggregating.

Nanoparticles find applications in fields ranging from healthcare, defense and day-to-day life. For these applications, stability and complete dispersibility of the nanoparticles in a solvent is essential, yet difficult to achieve. As such, widespread application is limited.

Thus, a method of synthesizing nanoparticles using a plant extract solving the aforementioned problems is desired.

SUMMARY OF THE INVENTION

A method of synthesizing nanoparticles using a plant extract can include providing a first solution including a metal salt or a metal oxide, providing a second solution including extract from orange peel, and combining the first solution and the second solution to produce a nanoparticle solution including metal nanoparticles or metal oxide nanoparticles. The nanoparticle solution can be used to produce a crystal nanoparticle powder, a non-crystal nanoparticle powder, and/or a metal-polymer nanocomposite. The polymer can be polystyrene (PS) or poly-vinyl alcohol (PVA).

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
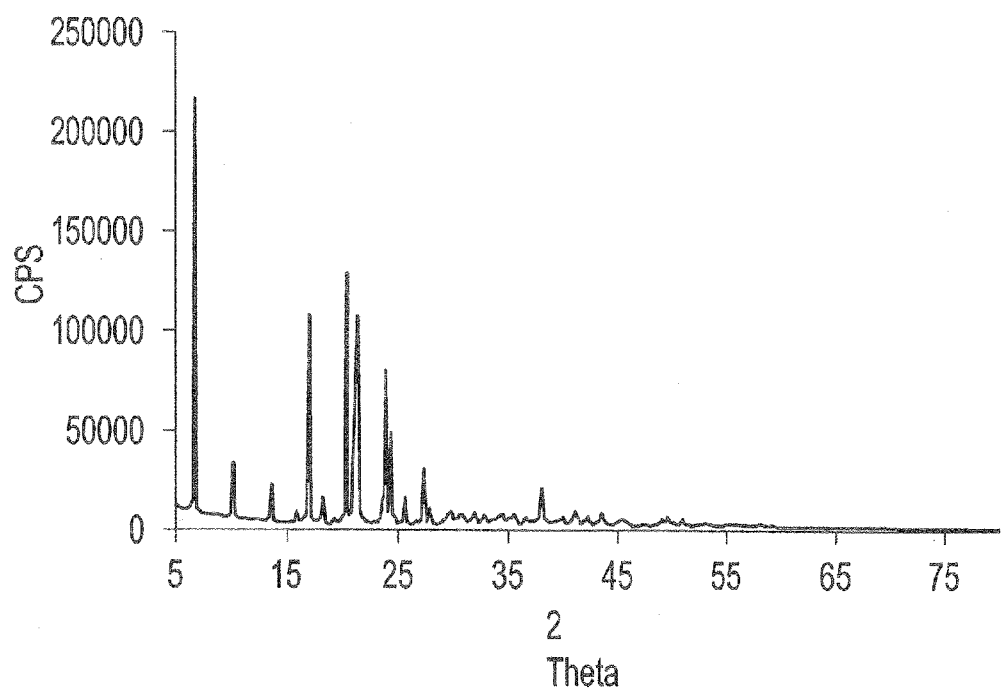
FIG. 1 shows a graph of X-ray powder diffraction (XRD) spectrum of green silver nanoparticles in solid state synthesized by the inventive method described in Example 2.

A method of synthesizing nanoparticles using a plant extract can include providing a first solution comprising a metal salt or a metal oxide, providing a second solution including extract from a plant, and combining the first solution and the second solution to produce a nanoparticle solution including metal nanoparticles or metal oxide nanoparticles. The extract from a plant can be extract from orange peel. The metal nanoparticles can be silver nanoparticles. The metal oxide nanoparticles can be titania nanoparticles. The nanoparticle solution can be used to produce crystal nanoparticle powder, non-crystal nanoparticle powder, and metal-polymer nanocomposites or metal containing nanoparticle-polymer composites wherein the polymer is polystyrene (PS) or poly-vinyl alcohol (PVA).

For synthesis of silver nanoparticles, the first solution can include a metal salt such as silver nitrate ($AgNO_3$). For synthesis of titanium dioxide ($TiO_2$) nanoparticles, the first solution can include a metal oxide such as titanium (IV) isopropoxide.

The second solution can include orange peel extract that is prepared in any suitable manner. For extraction with toluene, for example, orange peel, e.g., about 200 mg, can be crushed and mixed with toluene, e.g., about 20 ml, to form the second solution. The second solution can be stirred at a temperature of about 60° C. for about ten minutes, then centrifuged for about five minutes at about 7000 rpm at room temperature. For extraction with water, for example, orange peel, e.g., about 300 mg, can be washed and cut into small pieces. The orange peel pieces can be boiled in water, e.g., 50 ml, for about three minutes then filtered or centrifuged for about five minutes at about 7000 rpm at room temperature to form the second solution. The second solution can further include extract obtained from *Acacia nilotica*.

Combining the first solution and the second solution can include mixing the first solution with the second solution at a temperature of about 20° C. to about 40° C. for about ten minutes to about fifteen minutes. The first solution and/or the second solution can include toluene. The first solution and/or the second solution can be aqueous solutions. The metal or metal oxide nanoparticles can have a mean diameter in the range of from about 5 nm to about 100 nm. The metal or metal oxide nanoparticles can be spherical-shaped, spheroidal-shaped, elongated/spherical shaped, rod-shaped and/or faceted shaped.

A nano-composite film can be formed by mixing the nanoparticle solution with a polymer, such as polystyrene or poly vinyl alcohol (PVA). For example, the nanoparticle solution and the polymer can be stirred vigorously at a temperature of about 60° C. until the polymer is completely dissolved to form a third solution. The third solution can be transferred to a flat vessel or container, for example a glass plate, to allow the solvent in the solution to evaporate at room temperature. A nano-composite film can form once the solvent has evaporated.

As used herein the term "nanoparticle" refers to a particle having at least one dimension sized between 1 and 100 nanometers.

As used herein, the term "polymer" refers a large molecule composed of repeating structural units typically connected by covalent chemical bonds. The repeating structural units are monomer residues of one or more monomers that have undergone polymerization reaction form the polymer.

One way of protecting nanoparticles and increasing their solubility is by polymer stabilization. Polymer stabilization enhances the stability and processability of the nanoparticles to a great extent for industrial applications. Use of a polymeric solution can help provide a nano-composite system in which the metallic particles are homogeneously dispersed.

The polymer-metal nano-composite thin films described herein can facilitate efficient immobilization of the nanoparticles in the polymer matrix, are amenable to coating on surfaces of varying shapes and sizes, extensive reuse, and monitoring through successive action cycles. The metal nanoparticles can be generated within polymer films in situ to provide such nano-composite thin films.

The present methods can provide organic soluble nanoparticle-polymer composites in a simple manner and avoids the use of costly chemicals. The nanoparticle-polymer composites can be used in a variety of applications. For example, the nanoparticle-polymer composites can be used in food packaging and water packaging to increase and enhance the preservation of food and preserving the quality of water over long periods. The nanoparticle-polymer composites can be used as a membrane for water purification and desalination industries. The nanoparticle-polymer composites have several medical applications, including bandages and dressings for wounds to accelerate the healing of wounds and burns, and medical devices.

As demonstrated by the examples below, the aqueous extract of orange peel can be used to produce silver and titanium dioxide nanoparticles in a manner which is environmentally benign ("green"). The present inventors have further developed a simple in situ technique for the green fabrication of silver nanoparticle-embedded poly (vinyl alcohol) (Ag-PVA) thin film, and provides free-standing films. In situ generation of metal nanoparticles within polymer films is a particularly efficient approach to producing such nanocomposite thin films. The method can include use of an aqueous medium, deployment of the bio-compatible and bio-degradable polymer itself as the reducing agent, and soft-chemical synthesis involving mild thermal annealing for generating metal nanoparticles in situ inside the polymer matrix which serves as the stabilizer as well.

These nano-composite thin films possess utility in a wide range of areas, including optical limiting, microwave absorption, random lasers, e-beam lithography, non-volatile memory devices, catalysis and sensing has been demonstrated; significance of multiple reuse has been especially demonstrated in the catalytic application. Among the several avenues where bactericides find utility, purification of drinking water is one of the most critical and important areas. The metal nanoparticle solution and the metal-polymer nanocomposites have wide applications, for example, as an antibacterial agent, a sterilizer, food and water packaging, and in bandages for wound dressing.

The following examples will further illustrate the synthetic processes of making the green nanoparticle and the nanocomposite.

Example 1

Green Synthesis of Silver Nanoparticles

Figure 3:
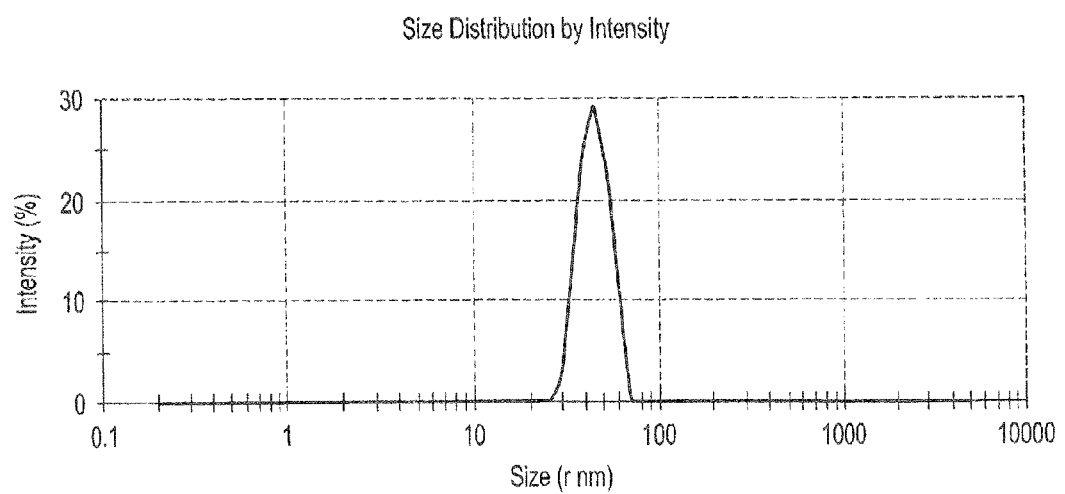
FIG. 3 shows a graph the average particle size (measured using a Zeta sizer) of the silver nanoparticles in liquid synthesized by the inventive method described in Example 1.
Figure 7:
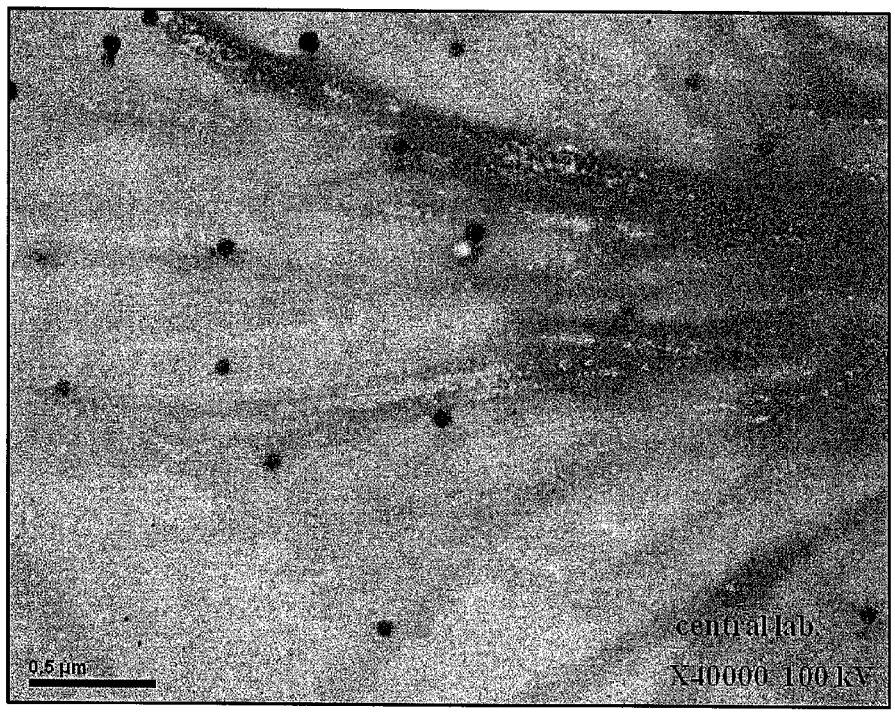
FIG. 7 shows the TEM image of AgNPs and AgNPs/PS nanocomposite film (the green silver nanoparticles were synthesized by the inventive method described in Example 1).
Figure 9:
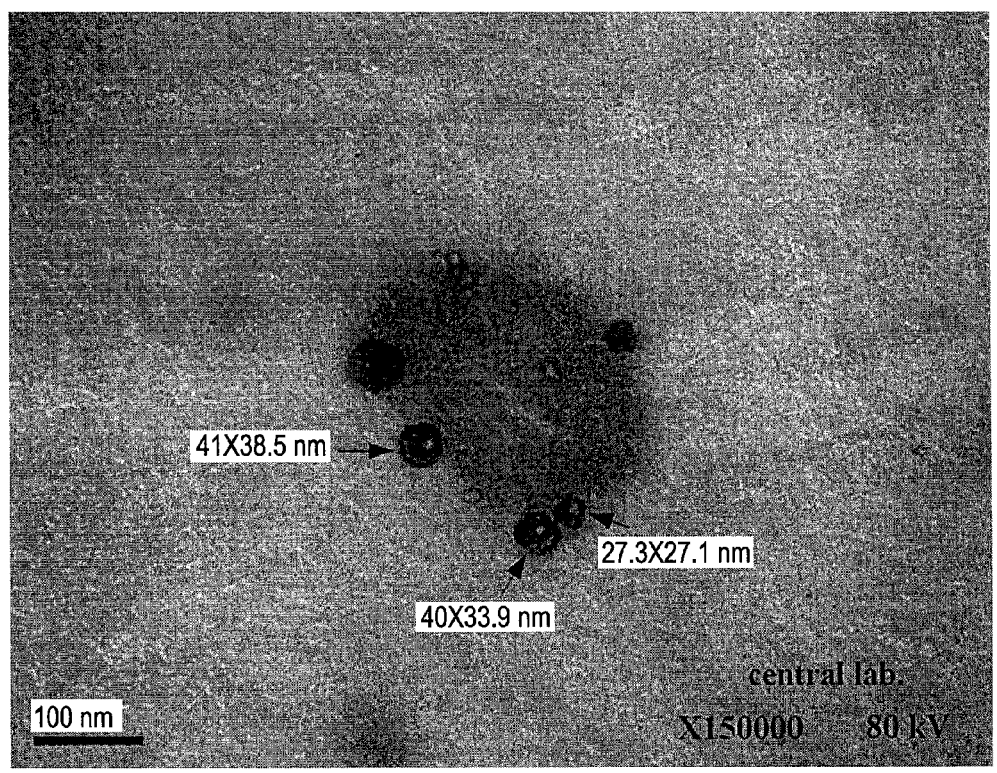
FIG. 9 shows the TEM image of green synthesis of silver nanoparticles using orange peel extracted by toluene (AgNPs).

About 200 mg of orange peel was crushed. The crushed orange peel was added to 20 ml of toluene in a flask, stirring vigorously for 10 minutes at 60° C. The toluene orange peel extract obtained was then centrifuged for 5 minutes at 7000 rpm at room temperature. Next, 1 mmole/ml silver nitrate ($AgNO_3$) was dissolved in 20 ml of toluene under vigorous stirring at 700° C. for 5 minutes. About 5 ml of orange peel extract was added to the solution of silver nitrate resulting in a color change. A brown solution was obtained, indicating reduction of Ag ions and the formation of silver nanoparticles. FIG. 3 shows a graph of the average particle size of the synthesized silver nanoparticles measured using a Zeta sizer. FIG. 7 shows the TEM image of green silver nanoparticles (AgNPs) and green silver nanoparticles/Polystyrene (AgNPs/PS) nanocomposite film. FIG. 9 shows the TEM image of green synthesis of silver nanoparticles using orange peel and toluene (AgNPs). The shapes of the nanoparticles typically appear as spherical and elongated spherical. However, the nanoparticle is not limited to spherical shapes but can possess various shapes such as rods and faceted shapes, etc.

Example 2

Figure 2:
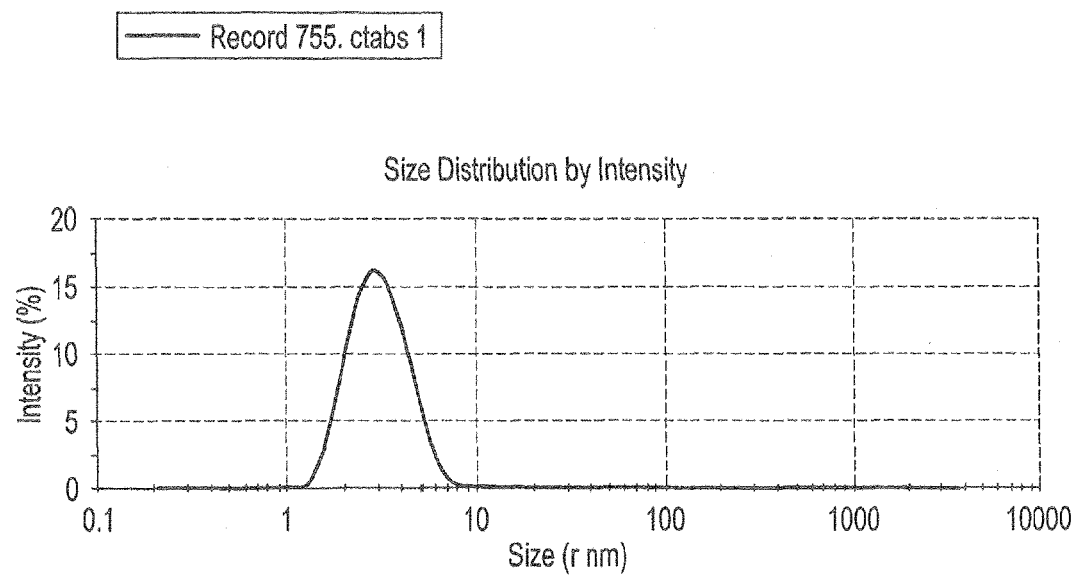
FIG. 2 shows a graph of the average particle size (measured using a Zeta sizer) of the silver nanoparticles in solid state synthesized by the inventive method described in Example 2.
Figure 4A:
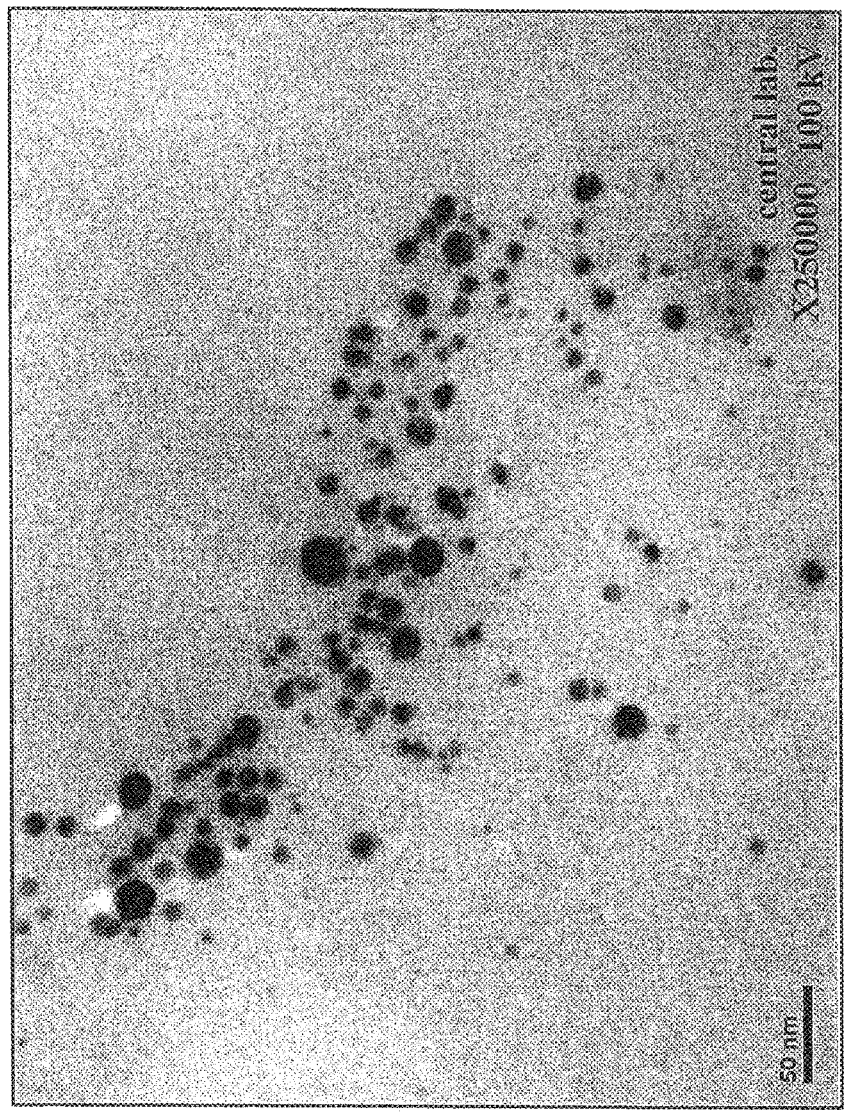
FIGS. 4A, 4B and 4C each show a graph of transmission electron microscopy (TEM) image of silver nanoparticles synthesized by the inventive method described in Example 2 (100 KV) with different shapes and magnifications.
Figure 4B:
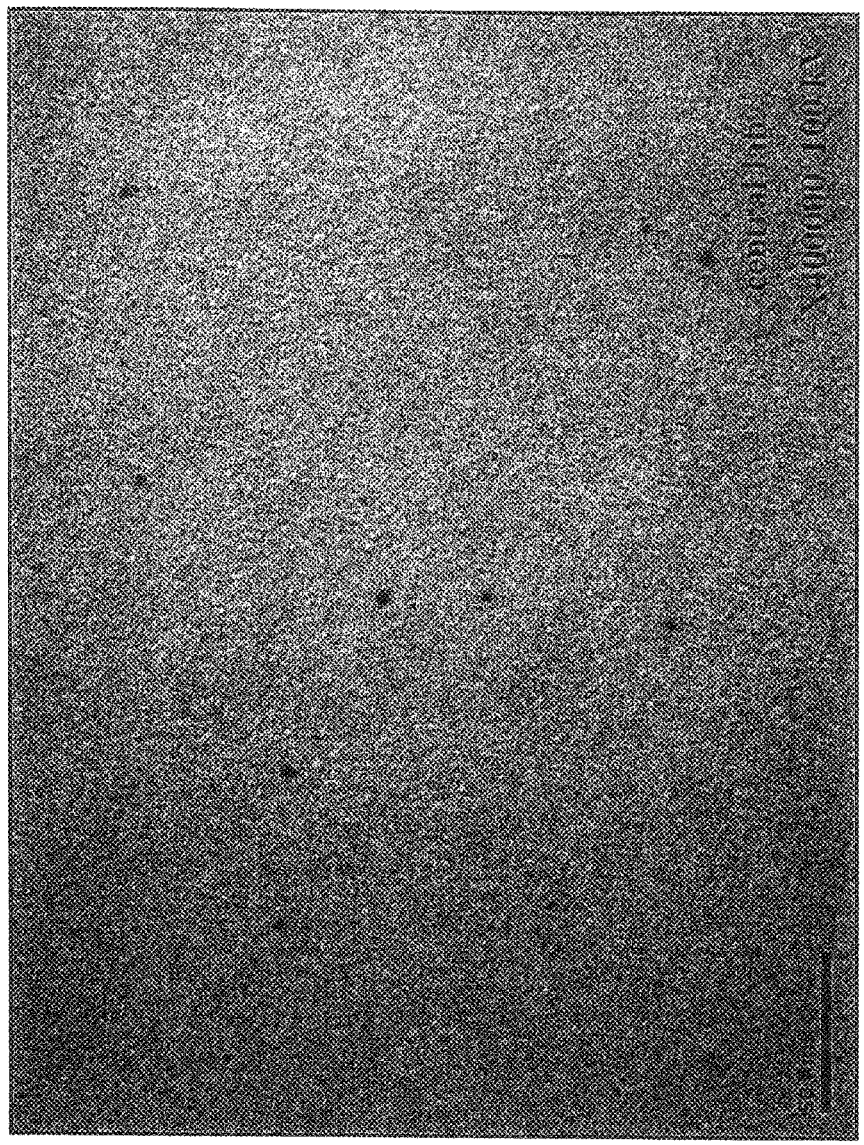
Figure 4C:
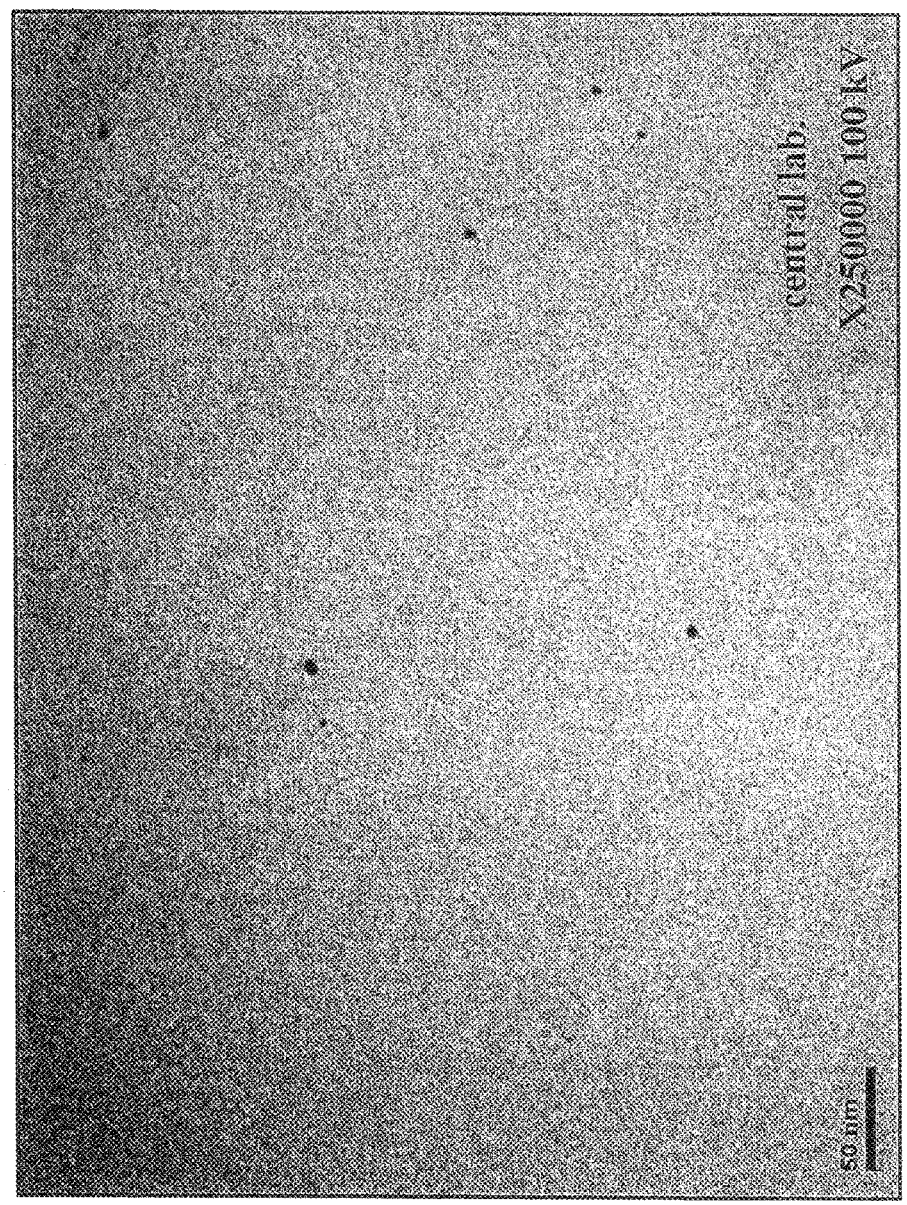

Green Synthesis of Silver Nanoparticles 300 mg of Orange peel was washed and cut into small pieces, boiled with 50 ml of distilled water for 3 minutes then filtered or centrifuged for about five minutes at about 7000 rpm at room temperature. Green silver nanoparticles were synthesized by adding 7 ml aqueous solution of orange peel extract to the aqueous solution of $2.0 \times 10^{-3}$ mole/L silver nitrate ($AgNO_3$) and $5.0 \times 10^{-4}$ mole/L (CTAB) cetyltrimethylammonium bromide under vigorous stirring at temperature 40° C. for 13 minutes at room temperature. The solution is free of color at this point. When adding the organic peel extract, the color changed from colorless to brown color. The color change indicated the formation of the respective bio nanosilver, which was then dried by air to produce bio-nanosilver crystal powder. FIG. 1 shows a graph of X-ray powder diffraction (XRD) spectrum of the synthesized silver nanoparticles in solid state. FIG. 2 shows a graph of the average particle size of the synthesized silver nanoparticles measured using a Zeta sizer. FIG. 4A depicts the Transmission Electron Microscopy (TEM) image at (150000× magnification) of the synthesized silver nanoparticles. FIG. 4B shows the Transmission Electron Microscopy (TEM) image at (300000× magnification) of the synthesized silver nanoparticles. FIG. 4C shows the Transmission Electron Microscopy (TEM) image at (250000× magnification) of the silver nanoparticles.

Example 3

Green Synthesis of Titania Nanoparticles

Figure 6:
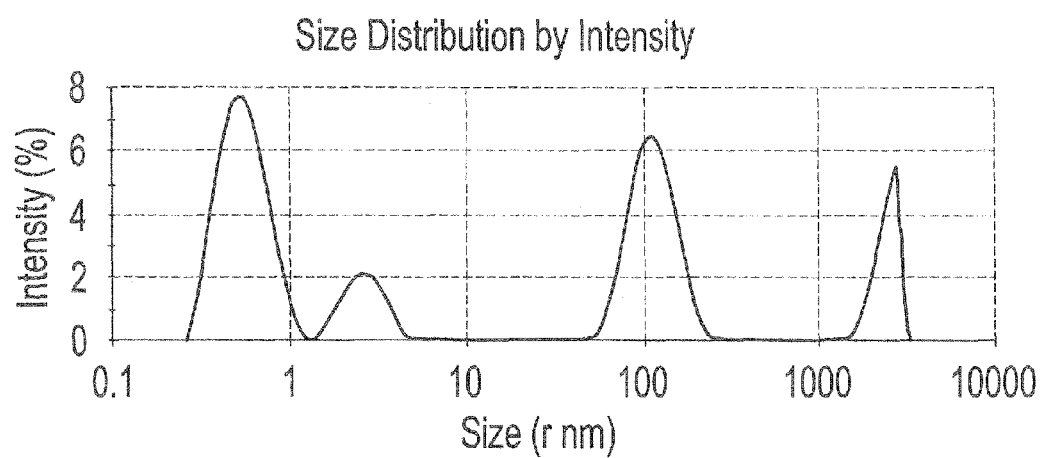
FIG. 6 presents a graph of the average size distribution by intensity of green titanium dioxide ($TiO_2$) nanoparticles prepared according to the present teachings.

About 300 mg of orange peel was washed and cut into small pieces and boiled with 50 ml) distilled water for 3 min then filtered or centrifuged for about five minutes at about 7000 rpm at room temperature. About 15 g of *Acacia Nilotica* herbal medical plant husk was soaked in 200 ml of distilled water overnight, filtered and then the aqueous extract was set aside until further use. The aqueous extract and titanium (IV) isopropoxide were mixed together at a molar ratio of 2:1 under vigorous stirring at temperature 30° C. for 10 minutes. The solution was transferred into a Teflon autoclave and/or oven at 300° C. for 7 hours yielding $TiO_2$ nanoparticles brownish powder (with *Acacia Nilotica* herbal medical plant extract and light yellow powder with orange peel extract), which was isolated by conventional filtration methods. FIG. 6 presents a graph of the average size distribution by intensity of green titanium dioxide ($TiO_2$) nanoparticles prepared according to the procedure of Example 3.

Example 4

Synthesis of Green Silver Nanoparticles/Polystyrene Nanocomposite Film

About 2 g of Polystyrene (PS) was added to the green silver nanoparticles that dispersed in toluene, and synthesized as described in Example 1. The solution was stirred under vigorous stirring at 60° C. until PS completely dissolved. Then the solution was cast in a glass plate and the solvent toluene was allowed to evaporate at room temperature to produce the nano-composite film. The film was removed from the glass plate after 24 hours. FIG. 7 shows the TEM image of AgNPs and AgNPs/PS nano-composite film.

Example 5

Synthesis of Green Silver Nanoparticles/Polystyrene Nano-Composite Film

Figure 5A:
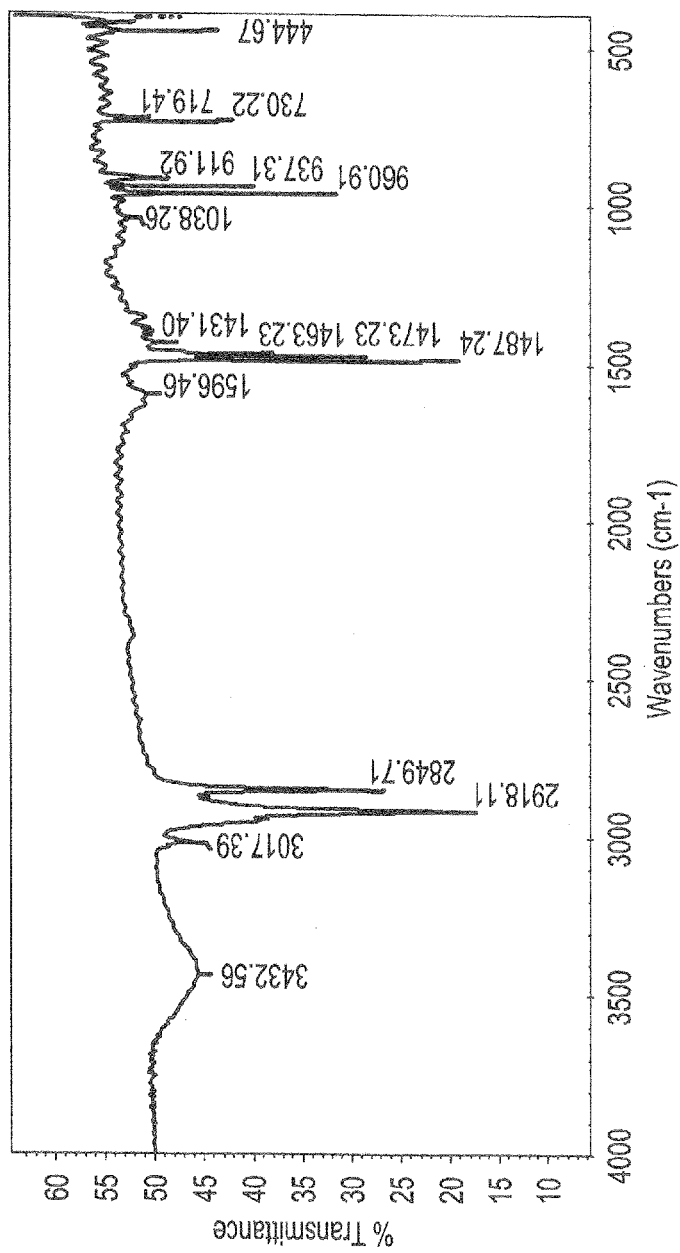
FIG. 5A shows a graph of FTIR spectrum of the silver nanoparticles in the powder form synthesized by the inventive method described in Example 2.
Figure 5B:
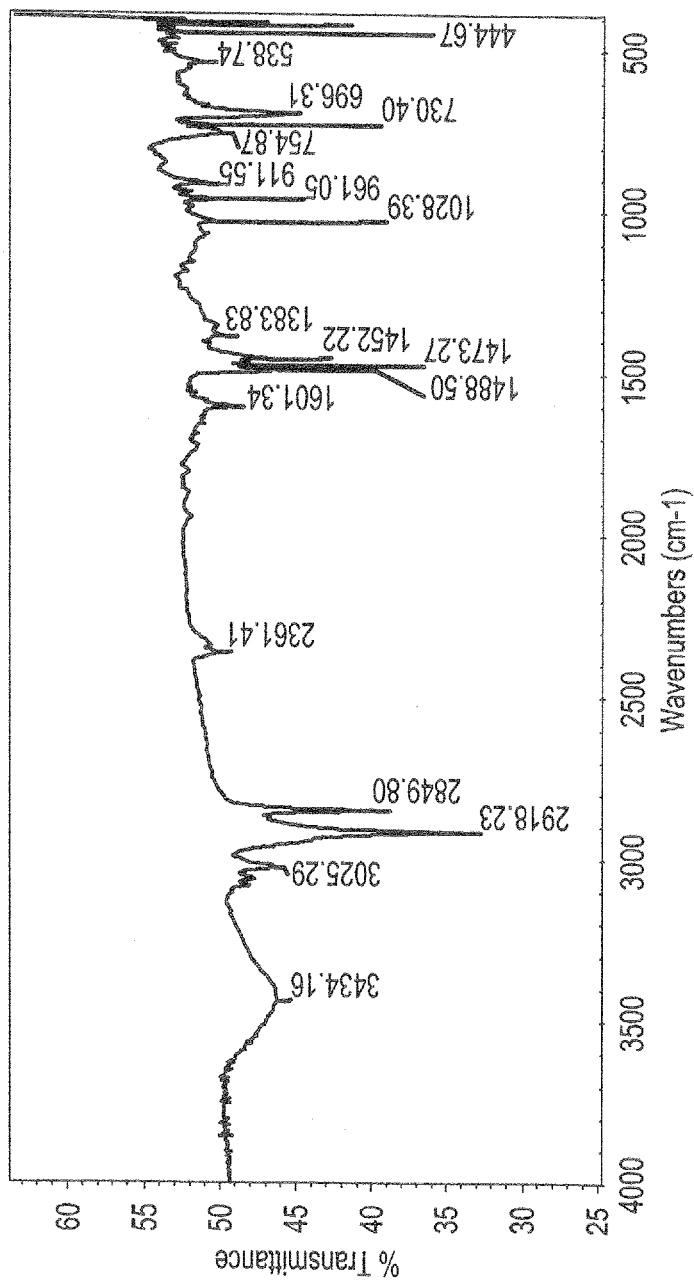
FIG. 5B shows a graph of FTIR spectrum of the silver-polymer nanocomposite synthesized in accordance with the present teachings.
Figure 8A:
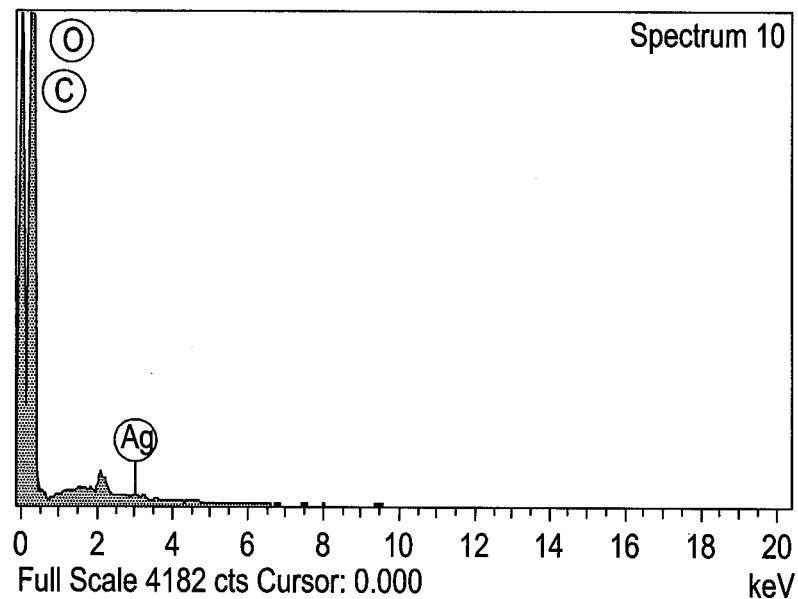
FIG. 8A shows elemental analysis by energy-dispersive spectroscopy (EDS) of the inventive green silver nanoparticles/PVA polymer nanocomposite.
Figure 8B:
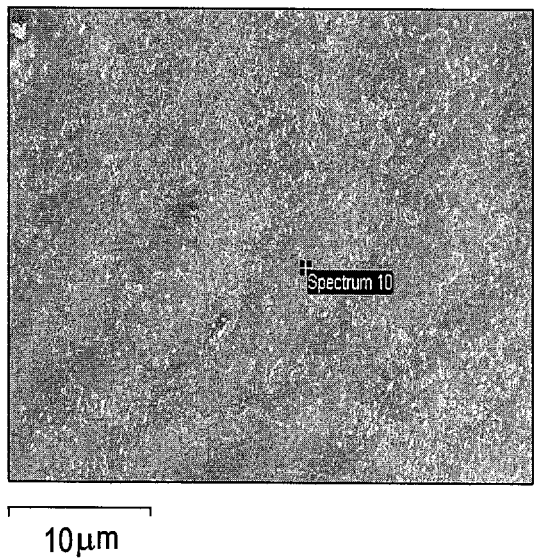
FIG. 8B shows the graph of scanning electron microscopy (SEM) image of the inventive green silver nanoparticles/PVA polymer nanocomposite.

The nanoparticles-PVA polymer film was prepared by adding 5 g of PVA to 50 ml of water under constant stirring at 50° C. until all PVA polymer dissolved. About 0.5 mg green nano-silver powder was dissolved in 3 ml water then it was added to the polymer solution and continuously stirred until completely mixed. The solution was then cast in a glass plate and left to dry resulting in green nanoparticles-PVA polymer film nanocomposite. FIG. 5A shows a graph of FTIR spectrum of green silver nanoparticles in the powder form. FIG. 5B shows a graph of the FTIR spectrum of the green silver-polymer nanocomposite. FIG. 8A shows elemental analysis by energy-dispersive spectroscopy (EDS) of the inventive green silver-polymer nanocomposite. FIG. 8B shows the graph of scanning electron microscopy (SEM) image of the inventive green silver-polymer nanocomposite.

Example 6

Antimicrobial Activity of Green Nanoparticle/Polymer Film Using Disc Diffusion Assay Pure culture of *Escherichia coli, Staphylococcus* and *Streptococcus* of bacteria were used. Nutrient agar medium plates were prepared, sterilized and solidified. After solidification, bacterial cultures were swabbed on these plates. The sterile discs were dipped in bio crystalline nano-silver powder (5, 10, 15 µg/ml) and/or small piece of green nanoparticles—polymer film with different concentrations (0.5, 1, and 2 mg) were placed in plate culture, and placed in the nutrient agar plate and kept for incubation at 37° C. for 24 hours. Upon inhibitory activity, a zone of clearing around the wells was observed. The diameter of the clearing zones was measured in mm using the ruler scale. These experiments were repeated three times and mean values of zone diameter were presented.

Example 7

Antimicrobial Activity of Green Nanoparticle/Polymer Film Using Disc Diffusion Assay The antibacterial activity of (AgNPs/PS) nano-composite was evaluated against Gram-negative bacteria *Escherichia coli* (*E. coli*) by a disc diffusion method. Nutrient agar medium plates were prepared, sterilized and solidified. After solidification bacterial cultures was swabbed on this plate. Then 0.5×0.5 cm from pure PS, 1% Ag NPs-PS nanocomposite film and 1 mmole/ml silver nanoparticles solution was placed in the nutrient agar plate and kept for incubation at 37° C. for 24 hours. Zones of inhibition were measured. The experiment was repeated 3 times for the sample and mean values of zone diameter were determined.

It is to be understood that the present invention is not limited to the embodiments described above, but encompasses any and all embodiments within the scope of the following claims.

We claim:

1. A method of synthesizing nanoparticles using a plant extract comprising:
   providing a first solution comprising a metal salt or a metal oxide;
   providing a second solution comprising extract from orange peel, wherein the second solution further includes extract obtained from *Acacia nilotica*, and
   combining the first solution and the second solution to produce a nanoparticle solution including metal nanoparticles or metal oxide nanoparticles.

2. The method of synthesizing nanoparticles using a plant extract according to claim 1, wherein:
   combining the first solution and the second solution comprises mixing the first solution with the second solution at a temperature of about 20° C. to about 40° C. for about ten minutes to about fifteen minutes.

3. The method of synthesizing nanoparticles using a plant extract according to claim 1, wherein the metal salt is silver nitrate (AgNO3) and the metal nanoparticles are silver nanoparticles.

4. The method of synthesizing nanoparticles using a plant extract according to claim 1, wherein the first solution and/or the second solution include toluene.

5. The method of synthesizing nanoparticles using a plant extract according to claim 1, wherein the first solution and/or the second solution are aqueous solutions.

6. The method of synthesizing nanoparticles using a plant extract according to claim 1, wherein the metal oxide is titanium (IV) isopropoxide and the metal oxide nanoparticles are titanium dioxide (TiO2) nanoparticles.

7. The method of synthesizing nanoparticles using a plant extract according to claim 1, wherein said metal or metal oxide nanoparticles have a mean diameter in the range of from about 5 nm to about 100 nm.

8. The method of synthesizing nanoparticles using a plant extract according to claim 1, wherein said metal or metal oxide nanoparticles have one or more shapes selected from the group consisting of spherical-shaped, spheroidal-shaped, elongated/spherical shaped, rod-shaped and faceted shaped.

* * * * *